US 6,566,314 B1
May 20, 2003

(12) United States Patent
Murthy et al.

(10) Patent No.: US 6,566,314 B1
(45) Date of Patent: May 20, 2003

(54) PERSONAL CLEANSING COMPOSITION AND METHOD

(75) Inventors: Usha V. Murthy, Oak Brook, IL (US); Dipak K. Ghosh, Woodridge, IL (US); Randy Schueller, Park Ridge, IL (US)

(73) Assignee: Alberto-Culver Company, Melrose Park, IL (US)

( * ) Notice: Subject to any disclaimer, the term of this patent is extended or adjusted under 35 U.S.C. 154(b) by 0 days.

(21) Appl. No.: 09/687,282

(22) Filed: Oct. 13, 2000

Related U.S. Application Data

(62) Division of application No. 09/361,366, filed on Jul. 26, 1999, now Pat. No. 6,365,559.

(51) Int. Cl.$^7$ ............................. A61K 7/50; C11D 1/12; C11D 1/90
(52) U.S. Cl. .................. 510/131; 510/101; 510/123; 510/125; 510/127; 510/159; 510/384; 510/391; 510/426; 510/495; 510/504; 424/401; 424/70.5; 424/70.122; 424/70.21; 424/70.22; 424/70.24; 424/70.27; 424/70.28
(58) Field of Search ..................... 510/101, 123, 510/125, 127, 131, 159, 384, 391, 426, 495, 504; 424/401, 70.5, 70.122, 70.21, 70.22, 70.24, 70.27, 70.28

(56) References Cited

U.S. PATENT DOCUMENTS

| | | | |
|---|---|---|---|
| 4,272,515 A | 6/1981 | Hofman et al. | 424/70 |
| 4,375,421 A | 3/1983 | Rubin et al. | 252/110 |
| 4,764,365 A | 8/1988 | Boothe et al. | 424/81 |
| 4,933,176 A | 6/1990 | van Reeth | 424/70 |
| 4,992,266 A * | 2/1991 | Knoll | 424/70 |
| 5,145,607 A | 9/1992 | Rich | 252/547 |
| 5,149,522 A | 9/1992 | Schwarz et al. | 424/70 |
| 5,290,482 A | 3/1994 | Marschner et al. | 252/544 |
| 5,326,483 A | 7/1994 | Halloran et al. | 252/174.15 |
| 5,478,490 A | 12/1995 | Russo et al. | 252/153 |
| 5,534,265 A | 7/1996 | Fowler et al. | 424/489 |
| 5,536,332 A * | 7/1996 | Chun | 132/202 |
| 5,540,853 A | 7/1996 | Trinh et al. | 510/101 |
| 5,641,480 A | 6/1997 | Vermeer | 424/70.24 |
| 5,653,970 A | 8/1997 | Vermeer | 424/70.24 |
| 5,658,577 A | 8/1997 | Fowler et al. | 424/401 |
| 5,720,961 A | 2/1998 | Fowler et al. | 424/401 |
| 5,730,965 A | 3/1998 | Rapaport | 424/70.1 |
| 5,753,245 A | 5/1998 | Fowler et al. | 424/401 |
| 5,767,051 A | 6/1998 | Drapier | 510/235 |

FOREIGN PATENT DOCUMENTS

| | | | |
|---|---|---|---|
| GB | 1567742 | * | 5/1980 |
| WO | WO 95/02389 | * | 1/1995 |

* cited by examiner

Primary Examiner—Mark Kopec
Assistant Examiner—Brian P. Mruk
(74) Attorney, Agent, or Firm—Leydig, Voit & Mayer, Ltd.

(57) ABSTRACT

An aqueous foam producing personal cleansing composition is disclosed. The composition, which is normally clear and is essentially free of any amides of diethanolamine, comprises a cloud point depressing agent comprising ammonium chloride. The composition of the present invention is characterized by a low cloud point temperature such that the risk of forming an undesirable precipitate in the composition is reduced. Also disclosed is a method of reducing the cloud point temperature in a normally clear aqueous personal cleansing composition which is essentially free of amides of diethanolamine. The method comprises adding ammonium chloride to the composition.

18 Claims, No Drawings

PERSONAL CLEANSING COMPOSITION AND METHOD

CROSS-REFERENCE TO RELATED APPLICATIONS

This application is a divisional application of U.S. application Ser. No. 09/361,366, filed on Jul. 26, 1999, which issued on Apr. 2, 2002, as U.S. Pat. No. 6,365,559.

TECHNICAL FIELD OF THE INVENTION

The present invention relates generally to personal cleansing compositions, including shampoos. In particular, the present invention relates to an aqueous personal cleansing composition which is transparent and which exhibits a reduced cloud point temperature.

BACKGROUND OF THE INVENTION

A wide variety of personal cleansing products have included amides of diethanolamine (such as, for example, cocamide diethanolamine), which function as stabilizers, emulsifiers, and/or foaming agents in such products. Amides of diethanolamine are also effective in depressing the cloud point temperature of transparent formulations in which they are included. As a result, the onset of a cloudy appearance caused by formation of precipitates in such conventional compositions occurs only at low temperatures (e.g., 4° C. or below). Cleansing compositions exhibiting such low cloud point temperatures are particularly desirable because they remain transparent over an extended temperature range and are therefore aesthetically pleasing to consumers. Indeed, undesirable precipitate formation, which diminishes the transparency of the compositions, is avoided under most conditions in compositions containing amides of diethanolamine.

Despite these advantages, products that include amides of diethanolamine are no longer entirely satisfactory in view of studies which have implicated diethanolamine as a cancer-causing ingredient in laboratory animals. Such study results may affect the purchase decisions of consumers, who have a proclivity to avoid products that may be linked to cancer. Although research efforts studying whether there is any connection between amides of diethanolamine and cancer have been inconclusive to date, consumers are increasingly seeking alternative cosmetic products which do not contain amides of diethanolamine in their formulations.

Nevertheless, it has been very difficult to develop alternative cleansing products that are free of amides of diethanolamine without compromising the desired functionality and/or aesthetics of the products, especially with respect to products that are normally transparent. For example, many cleansing compositions that are free of diethanolamine (e.g., those products that contain sodium lauryl sulfate as an anionic cleansing agent) are characterized by undesirably higher cloud point temperatures (e.g., 12° C.), as compared with conventional cleansing compositions that contain amides of diethanolamine. Often, cleansing product formulations that are free of amides of diethanolamine have a cloud point temperature that is significantly higher (e.g., by 50% or more) than the cloud point temperature found in corresponding formulations that contain amides of diethanolamine.

As a result, many formulations that exclude amides of diethanolamine are ill-suited for practical use. While such compositions may be normally clear and aesthetically pleasing to consumers at a temperature above the cloud point temperature, for example, at room temperature, the relatively high cloud point temperature of such formulations (which are generally closer to room temperature than formulations that contain amides of diethanolamine) render those compositions more susceptible to precipitate formation such that the transparency of the compositions would diminish. Because of the increased risk that such compositions would be subjected to a temperature below the cloud point temperature, such as, for example, during storage, when transported, or the like, precipitate formation may be more apt to occur such that the product would become aesthetically unappealing, thereby leading to consumer rejection. As a related complication, conventional cleansing compositions that are not stabilized with an amide of diethanolamine also exhibit an undesirably high "recovery time," that is, the amount of time required for a composition that has been chilled to a temperature below its cloud point to return to a clear appearance upon reaching a temperature above its cloud point. Often, such compositions require several hours to reassume a normally clear appearance.

Accordingly, it will be appreciated that there exists a need in the art for a transparent personal cleansing composition which is free of amides of diethanolamine and which does not suffer from an undesirably high cloud point temperature. There is also a need for a personal cleansing composition which, in the unwanted event that the composition is subjected to an environment in which the temperature is at or below the cloud point temperature, rapidly recovers its normally transparent appearance upon reaching a temperature above its cloud point temperature. These and other objects and advantages of the present invention, as well as additional inventive features, will be apparent from the description of the invention provided herein.

BRIEF SUMMARY OF THE INVENTION

The present invention provides a normally clear personal cleansing composition which is essentially free of amides of diethanolamine and which is characterized by a desirably low cloud point temperature. The composition of the present invention comprises water and a cloud point depressing agent comprising ammonium chloride.

The present invention also provides a method of reducing the cloud point temperature in a normally clear aqueous personal cleansing composition which is essentially free of amides of diethanolamine. The method comprises adding ammonium chloride to the composition.

Advantageously, the present invention permits the exclusion of amides of diethanolamine in a cleansing composition without causing the composition to have an undesirably high cloud point temperature. As a result, not only is the composition nontoxic and safe for consumer use in cleansing products, but also the risk of forming an undesirable precipitate in the composition, including, for example, during storage and/or transportation conditions, is attenuated in view of the reduced cloud point temperature exhibited by the composition. Moreover, even in the unwanted event that the composition is exposed to temperatures at or below the composition's cloud point temperature, the composition is characterized by a relatively short recovery time for returning to clarity upon reaching a temperature above the cloud point temperature after being chilled to a temperature below the cloud point temperature. As such, the present invention provides a cleansing composition with enhanced stability and which is aesthetically pleasing.

DETAILED DESCRIPTION

The present invention is predicated, at least in part, on providing a normally clear cleansing composition which is essentially free of amides of diethanolamine and which has a desirably low cloud point temperature. In particular, the composition comprises water and a cloud point depressing agent comprising ammonium chloride. Surprisingly, in accordance with the present invention, by including ammonium chloride in the composition, it has been found that the cloud point temperature of the composition is reduced even though the composition is essentially free of any amides of diethanolamine. The composition can be used in personal products, such as, for example, shampoos and the like.

The inventive personal cleansing composition is aqueous. In this respect, the amount of water (diluent) in the composition can range, for example, from about 25% to about 80% by weight of the composition, preferably from about 40% to about 70% by weight of the composition, and even more preferably from about 50% to about 60% by weight of the composition.

The composition of the present invention also includes ammonium chloride, which serves to depress the cloud point temperature of the composition. Preferably, ammonium chloride is provided in an amount such that the composition exhibits a cloud point temperature of about 6° C. or below, more preferably about 4° C. or below, even more preferably about 2° C. or below, still more preferably about 0° C. or below, and even still more preferably about −2° C. or below. As alternative or additional features of the present invention, the ammonium chloride is preferably provided in an amount sufficient to reduce the cloud point temperature exhibited by the composition by at least about 20%, and more preferably by at least about 40%, as compared with a corresponding formulation absent the ammonium chloride; and/or the ammonium chloride is preferably in an amount sufficient to depress the cloud point temperature by at least about 8° C., and more preferably by at least about 10° C., as compared with a corresponding formulation absent the ammonium chloride.

In addition to its cloud point depressing feature, the ammonium chloride also advantageously serves as a thickener (i.e., viscosity enhancer) for the composition of the present invention. As a result, the inventive composition need not include any additional thickener, although an additional thickener can be added, if desired. The viscosity of the inventive composition is not narrowly critical, but compositions having a viscosity within a certain range are desirable because of enhanced consumer appeal. In this respect, the viscosity of the composition of the present invention preferably ranges from about 1,500 cps to about 20,000 cps, more preferably from about 2,000 cps to about 15,000 cps, and still more preferably from about 4,000 cps to about 8,000 cps.

Accordingly, as noted above, ammonium chloride is provided in the composition in an amount sufficient to depress the cloud point temperature of the composition, and it is also preferably provided in an amount sufficient to impart the composition with a desired viscosity, such as, for example, a viscosity within the preferred ranges described above. For example, ammonium chloride preferably is provided in the composition in an amount of from about 0.001% to about 5% by weight of the composition, more preferably in an amount of from about 0.01% to about 2% by weight of the composition, and even more preferably in an amount of from about 0.2% to about 0.5% by weight of the composition.

The composition also desirably includes at least one cleansing agent in an effective amount. By way of example, the composition can include a primary anionic cleansing agent, such as sodium lauryl sulfate. Significantly, previously known formulations that included sodium lauryl sulfate exhibited particularly high cloud point temperatures. However, the present invention permits the use of sodium lauryl sulfate inasmuch as the cloud point temperature is depressed by the inclusion of ammonium chloride in the inventive composition. Preferably, the composition also includes a secondary anionic cleansing agent, such as, for example, sodium laureth sulfate.

The primary anionic cleansing agent is preferably included in the composition in an amount of from about 5% to about 45% by weight of the composition, more preferably in an amount of from about 20% to about 40% by weight of the composition, and still more preferably in an amount of from about 25% to about 35% by weight of the composition. The secondary anionic cleansing agent, if any, can be included in the composition in an amount of from about 0.01% to about 10% by weight of the composition, more preferably in an amount of from about 0.05% to about 8% by weight of the composition, and still more preferably in an amount of from about 0.1% to about 5% by weight of the composition.

Aside from anionic cleansing agents, additional cleansing agents, such as, for example, one or more amphoteric cleansing agents (i.e., agents having both anionic and cationic portions) and/or other classes of tertiary cleansing agents, can be included in the inventive composition, if desired. Amphoteric cleansing agents are well known in the art. The presence of such additional cleansing agents is preferred in order to offer foam boosting such that the stability of the composition is enhanced and/or to promote the mildness of the composition. By way of example, preferred amphoteric cleansing agents that can be included in the inventive composition include, but are not limited to, one or more betaines, such as, for example, cocamidopropyl betaine. Also, other types of "non-anionic" cleansing agents which are also well known in the art can be included as alternatives or in addition to the amphoteric cleansing agents. For example, suitable cleansing agents can be selected from additional classes of cleansing agents such as, but not limited to, amine oxides, nonionic acyl polyglucosides, or combinations thereof.

These additional non-anionic cleansing agents, e.g., the amphoteric cleansing agents and/or other classes of cleansing agents such as amine oxides, nonionic acyl polyglucosides, and combinations thereof (as discussed above) can be included in any effective amount in the inventive composition. By way of example, these non-anionic cleansing agents preferably can be provided in an amount of from about 0.1% to about 20% by weight of the composition, more preferably in an amount of from about 0.5% to about 15% by weight of the composition, and even more preferably in an amount of from about 2% to about 10% by weight of the composition.

Although not essential, at least one preservative in any effective amount is useful in preferred personal cleansing compositions of the invention. The term "preservative," as used herein, includes preservative aids such as chelating agents. Examples of suitable preservatives and/or preservative aids include, for example, disodium EDTA, trisodium EDTA, tetrasodium EDTA, DMDM hydantoin, and combinations thereof. As will be appreciated by one of ordinary skill in the art, DMDM hydantoin is understood worldwide pursuant to the nomenclature for cosmetic products set forth in the International Cosmetic Ingredient Directory and Handbook. The chemical name for DMDM hydantoin is 1,3-dimethylol-5,5-dimethyl hydantoin, which is commercially available from Lonza, Inc. of Fairlawn, N.J. under the trade name "Glydant." Preferably, the preservative is provided in an amount of from about 0.001% to about 1.75% by weight of the composition, more preferably in an amount of from about 0.05% to about 0.4% by weight of the composition, and even more preferably in an amount of from about 0.1% to about 0.4% by weight of the composition.

The preservative included in the composition of the present invention preferably includes both a primary preservative (e.g., DMDM hydantoin) in conjunction with a chelating agent (e.g., tetrasodium EDTA, trisodium EDTA, disodium EDTA, or combinations thereof). The chelating agent not only helps to potentiate the efficiency of the primary preservative, it may also bind to metal ions that might be present in water used by a consumer. Inclusion of a chelating agent thus enhances the soaping/surfactant abilities of the cleansing agents present in the composition.

In some embodiments, the preservative includes tetrasodium EDTA and DMDM hydantoin in combination. In such embodiments, the tetrasodium EDTA is preferably present in an amount of from about 0.001% to about 1% by weight of the composition, more preferably in an amount of from about 0.01% to about 0.1% by weight of the composition, and even more preferably in an amount of from about 0.03% to about 0.07% by weight of the composition. In these embodiments, the DMDM hydantoin is preferably present in an amount of from about 0.01% to about 0.75% by weight of the composition, more preferably in an amount of from about 0.05% to about 0.4%, and still more preferably in an amount of from about 0.1% to about 0.4% by weight of the composition.

The personal cleansing composition of the present invention can have any suitable pH. Preferably, the inventive composition exhibits a pH of from about 3.5 to about 7.5, more preferably of from about 4 to about 6.5, and even more preferably of from about 4.5 to about 6.

If desired, the inventive composition can optionally include a pH adjuster in order to provide the composition with a pH within the preferred ranges. Examples of suitable pH adjusters include, but are not limited to, citric acid, lactic acid, phosphoric acid, hydrochloric acid, and combinations thereof. The pH adjuster, if included, can be provided in any effective amount. Preferably, the pH adjuster is included in the composition in an amount of from about 0.01% to about 0.5% by weight of the composition, more preferably in an amount of from about 0.05% to about 0.2% by weight of the composition, and even more preferably in an amount of from about 0.08% to about 0.15% by weight of the composition.

Other optional ingredients that may be useful in the personal cleansing composition of the present invention include, for example, hair strengtheners (e.g., proteins or protein derivatives), vitamins, conditioning agents (e.g., quaternary ammonium conditioning agents), fragrances, dyes, and combinations thereof. With respect to the hair strengthener, examples of this optional ingredient include, but are not limited to, hydrolyzed collagen, wheat, rice, soy, oat, silk and combinations thereof. If included, the hair strengthener desirably is present in an amount of from about 0.001% to about 2% by weight of the composition, more preferably of from about 0.01% to about 1.5% by weight of the composition, and even more preferably of from about 0.1% to about 1% by weight of the composition.

The inventive composition is normally clear, and can be colorless or colored as desired. Indeed, any of a number of suitable dyes and/or fragrances (e.g., fruity or floral) can also be included, if desired. If included, the optional dyes and/or fragrances preferably are present in an amount ranging from about 0.1% to about 2% by weight of the composition.

Examples of suitable vitamins and/or conditioning agents include, but are not limited to, vitamin E, vitamin A, vitamin C, provitamin B5, ergocalciferol, tocopherol, polyquat-7, polyquat-10, cocotrimonium chloride, and combinations thereof. If included, the vitamins and/or conditioning agents can be provided in any effective amount. For example, the conditioning agent can be included in the composition in an amount of from about 0.01% to about 2% by weight of the composition, more preferably in an amount of from about 0.5% to about 1.5% by weight of the composition, and even more preferably in an amount of about 1% by weight of the composition. Vitamins are preferably included in the composition in an amount of from about 0.0001% to about 0.01% by weight of the composition and more preferably in an amount of from about 0.0001% to about 0.0003% by weight of the composition.

Surprisingly, the composition of the present invention not only exhibits a depressed cloud point temperature, but the composition is also characterized by a recovery time which is faster than the recovery time of the composition absent the ammonium chloride cloud point depressing agent. The term "recovery time," as used herein, refers to the length of time required for the composition to return to its normally clear condition upon reaching a temperature above the cloud point temperature, after the composition has been chilled to a temperature below the cloud point temperature. Preferably, the recovery time exhibited by the inventive composition is no more than one-half of the recovery time exhibited by a corresponding composition absent the ammonium chloride subjected to the same conditions (e.g., subjected to the same temperature shifts), and more preferably the recovery time demonstrated by the inventive composition is no more than one-third the recovery time of a corresponding composition absent the ammonium chloride under the same conditions. In preferred embodiments, the composition according to the invention is characterized by a recovery time of less than 1 hour upon being subjected to room temperature, after the composition has been chilled below the cloud point.

The following Examples further illustrate the present invention, but, of course, should not be construed as in any way limiting its scope. Quantities are in percent by weight of the total composition, unless otherwise indicated.

EXAMPLE I

This Example illustrates an embodiment of the personal cleansing composition of the present invention. The formulation of this embodiment is set forth in Table I.

TABLE I

Exemplary Base Formula

| INGREDIENT | WEIGHT % |
|---|---|
| Deionized water | 62.6810 |
| Tetrasodium EDTA | 0.0400 |
| Citric Acid | 0.1140 |
| Dye | 0.3000 |
| Sodium Lauryl Sulfate | 28.0000 |
| Sodium Laureth Sulfate | 1.0000 |
| Cocamidopropyl Betaine | 6.5400 |
| DMDM Hydantoin | 0.2000 |
| Fragrance | 0.2250 |
| Ammonium Chloride | 0.9000 |
| Total | 100% |

In preparing the composition set forth in Table I, a first step involved adding deionized water, which was pre-heated to 125° F. (≈51.7° C.), to a large mixing tank supplied with a mixer.

In a second step, tetrasodium EDTA, citric acid, and the dye (in a 1% solution), were then added to the mixing tank while mixing continued. In a third step, sodium lauryl sulfate, sodium laureth sulfate, and cocamidopropyl betaine were then added to the mixing tank, and mixing continued such that all of the ingredients were dissolved and the batch was clear and homogenous.

In a fourth step, DMDM hydantoin was added to the composition and mixing continued until the batch was uniformly mixed. In a fifth step, the fragrance was added while mixing continued.

In a sixth step, ammonium chloride was premixed with deionized water, then added to the batch and mixed for at least 20 minutes. The water that is premixed with the ammonium chloride serves as a processing aid and is provided in an amount sufficient for dissolving the salt. It is to be noted that, alternatively, ammonium chloride may be directly added to the batch without pre-dissolution.

The completed composition exhibited a pH of 4.31, a viscosity of 4,850 cps, a specific gravity at 25° C. of 1.01, and a cloud point temperature of −1° C. In addition, the composition exhibited a recovery time of less than 10 minutes upon being subjected to room temperature after the composition had been chilled below the cloud point.

EXAMPLE II

This Example illustrates another embodiment of the personal cleansing composition of the present invention. The formulation of this exemplary embodiment is set forth in Table II.

TABLE II

Exemplary Base Formulation

| INGREDIENT | WEIGHT % |
|---|---|
| Deionized Water | 57.098 |
| Tetrasodium EDTA | 0.010 |
| Citric Acid | 0.300 |
| Dyes (1% Solution) | 0.046 |
| Sodium Lauryl Sulfate | 29.750 |
| Cocamidopropyl Amine Oxide | 4.200 |
| Cocamidiopropyl Betaine | 2.000 |
| Aloe Barbadensis Extract | 0.010 |
| Passionflower Extract | 0.010 |
| Ergocalciferol | 0.001 |
| DMDM Hydantoin | 0.200 |
| Fragrance | 0.750 |
| Deionized Water | 5.000 |
| Ammonium Chloride | 0.625 |
| Total | 100.000% |

This composition was prepared as generally described in Example I. In this respect, the dyes were added with tetrasodium EDTA and citric acid in the second step. Aloe Barbadensis Extract, Passionflower Extract and Ergocalciferol were added along with DMDM hydantoin in the fourth step (and mixed until the batch was uniformly mixed).

The completed composition had a pH of 4.9, a viscosity of 4,300 cps, a specific gravity at 25° C. of 1.01, and a clear honey-brown color. The composition also had a cloud point of 3° C. and a recovery time of about 10 minutes after being subjected to room temperature after having been chilled below the cloud point.

While this invention has been described with an emphasis upon certain preferred embodiments, it will be apparent to those of ordinary skill in the art that variations in the preferred compositions and methods may be used and that it is intended that the invention may be practiced otherwise than as specifically described herein. Accordingly, this invention includes all modifications encompassed within the spirit and scope of the invention as defined by the following claims.

What is claimed is:

1. A method of reducing the cloud point temperature in a normally clear aqueous personal cleansing composition that is essentially free of amides of diethanolamine so that the composition is non-toxic, wherein the composition comprises (a) water, (b) sodium lauryl sulfate, (c) an amphoteric cleansing agent, (d) at least one preservative, and, optionally, one or more of the following ingredients: (i) a protein or protein derivative, (ii) a dye, (iii) a fragrance, and (iv) a pH adjuster, said method comprising:

including ammonium chloride in said composition to reduce the cloud point in said composition to a temperature of about 6° C. or lower.

2. The method of claim 1, wherein said including of ammonium chloride reduces the cloud point in said composition by at least 40%.

3. The method of claim 2, wherein said including of ammonium chloride reduces the cloud point in said composition by at least 8° C.

4. The method of claim 1, wherein said including of ammonium chloride reduces the cloud point in said composition to a temperature of about 2° C. or lower.

5. The method of claim 4, wherein said including of ammonium chloride reduces the cloud point in said composition to a temperature of about 0° C. or lower.

6. The method of claim 1, wherein sodium lauryl sulfate is present in said composition in an amount of from about 5% to about 45% by weight of said composition.

7. The method of claim 1, wherein said composition further comprises sodium laureth sulfate.

8. The method of claim 7, wherein sodium laureth sulfate is present in said composition in an amount of from about 0.01% to about 10% by weight of said composition, and wherein the amphoteric cleansing agent is present in said composition in an amount of from about 2% to about 10% by weight of said composition.

9. The method of claim 1, wherein ammonium chloride is present in said composition in an amount of from about 0.001% to about 5% by weight of said composition.

10. The method of claim 1, wherein said preservative is selected from the group consisting of 1,3-dimethylol-5,5-dimethyl hydantoin, disodium EDTA, trisodium EDTA, tetrasodium EDTA, and combinations thereof.

11. The method of claim 1, wherein said composition further comprises agent.

12. The method of claim 11, wherein said chelating agent comprises tetrasodium EDTA, trisodium EDTA, disodium EDTA, or combinations thereof.

13. The method of claim 1, wherein said composition further comprises a pH adjuster, which is present in an amount sufficient to maintain the pH of said composition from about 3.5 to about 7.5.

14. The method of claim 1, wherein said composition further comprises a non-anionic cleansing agent.

15. The method of claim 14, wherein said non-anionic cleansing agent is selected from the group consisting of betaines, amine oxides, nonionic acyl polyglucosides, and combinations thereof.

16. The method of claim 1, wherein said amphoteric cleansing agent comprises cocamidopropyl betaine.

17. The method of claim 1, wherein said composition further comprises at least one additional component selected from the group consisting of vitamins, quaternary conditioning agents, and combinations thereof.

18. A method of reducing the cloud point temperature in a normally clear aqueous personal cleansing composition that is essentially free of amides of diethanolamine so that the composition is non-toxic, wherein the composition comprises (a) water, (b) sodium lauryl sulfate, (c) an amphoteric cleansing agent, (d) at least one preservative, and, optionally, one or more of the following ingredients: (i) a protein or protein derivative, (ii) a dye, (iii) a fragrance, and (iv) a pH adjuster, said method comprising:

including ammonium chloride in said composition, in an amount of from about 0.2% to about 0.5% by weight of said composition, to reduce the cloud point in said composition to a temperature of about 6° C. or lower.

* * * * *